(12) United States Patent
Ayalon et al.

(10) Patent No.: US 11,450,427 B1
(45) Date of Patent: Sep. 20, 2022

(54) COMPUTING SYSTEM FOR DISPLAYING LOCATIONS OF CLINICAL EVENTS UNDERGONE BY PATIENTS

(71) Applicant: Allscripts Software, LLC, Raleigh, NC (US)

(72) Inventors: Yaniv Ayalon, Metzadot Yehuda (IL); Dudu Avinoam, Beer Sheva (IL); Oz Carmel, Lahav (IL)

( * ) Notice: Subject to any disclaimer, the term of this patent is extended or adjusted under 35 U.S.C. 154(b) by 149 days.

(21) Appl. No.: 16/674,575

(22) Filed: Nov. 5, 2019

(51) Int. Cl.
   *G16H 40/20* (2018.01)
   *G16H 10/60* (2018.01)
   *G06Q 30/02* (2012.01)

(52) U.S. Cl.
   CPC ............ *G16H 40/20* (2018.01); *G16H 10/60* (2018.01); *G06Q 30/0205* (2013.01)

(58) Field of Classification Search
   CPC ..... G16H 40/20; G16H 10/60; G06Q 30/0205
   See application file for complete search history.

(56) References Cited

U.S. PATENT DOCUMENTS

| | | |
|---|---|---|
| 8,626,521 B2 | 1/2014 | Brown et al. |
| 2009/0319295 A1 | 12/2009 | Kass-Hout et al. |
| 2010/0131482 A1 | 5/2010 | Linthicum et al. |
| 2012/0290323 A1* | 11/2012 | Barsoum ................ G16H 15/00 705/3 |
| 2014/0108048 A1 | 4/2014 | Cohn |
| 2015/0095068 A1 | 4/2015 | Ryan et al. |
| 2017/0109493 A1* | 4/2017 | Hogg ..................... G16H 50/30 |
| 2018/0150611 A1* | 5/2018 | Hasan ................... G16H 10/60 |
| 2020/0342545 A1* | 10/2020 | Dobson ................. G16H 40/20 |

FOREIGN PATENT DOCUMENTS

JP          2014514679 A    *    5/2011    ............ G06Q 50/22

* cited by examiner

*Primary Examiner* — Sheetal R Paulson
(74) *Attorney, Agent, or Firm* — Calfee, Halter & Griswold LLP

(57) ABSTRACT

An agent application executing on a computing device identifies a patient health record for a patient based upon an identifier for the patient. The patient health record comprises an identifier for a healthcare facility at which a clinical event of the patient occurred and information about the clinical event. The agent application transmits the identifier for the healthcare facility to a mapping computing system that retrieves a map of an area encompassing the healthcare facility based upon the identifier for the healthcare facility. The map includes a marker that marks a location of the healthcare facility. Responsive to receiving the map, the agent application causes a graphical indicator to be included in the map proximate to the marker, the graphical indicator including the identifier for the healthcare facility and the information about the clinical event. The agent application causes the map to be displayed on a display.

20 Claims, 7 Drawing Sheets

COMPUTING SYSTEM FOR DISPLAYING LOCATIONS OF CLINICAL EVENTS UNDERGONE BY PATIENTS

BACKGROUND

Electronic health records (EHR) applications are computer-executable applications that are configured to assist healthcare workers with providing care to patients. EHR applications are configured with functionality pertaining to patient intake, patient billing, insurance billing, prescription generation, maintaining a record of patient care over time, etc. EHR applications are often used by healthcare workers at the point of care (i.e., at a time when the healthcare worker is providing care to a patient). For example, a healthcare worker may retrieve data from a patient health record maintained by an EHR application to relatively quickly ascertain problems being experienced by the patient, medications currently being taken by the patient, and so forth.

Agent applications are computer-executable applications that are also configured to assist healthcare workers with providing care to patients. However, unlike an EHR application which accesses patient health records from an electronic source (e.g., a database of the EHR application) under control of a single healthcare organization, agent applications are configured to access (and optionally store) patient health records from a plurality of electronic sources that may be under control of different healthcare organizations. For instance, the plurality of electronic sources may include different EHR applications, health information exchanges (HIEs), and so forth.

As an agent application is able to access patient health records for a patient from a plurality of electronic sources (e.g., different EHR applications), the agent application may display identifiers for healthcare facilities at which clinical events (e.g., undergoing a procedure, visiting a physician, being prescribed a medication, etc.) of the patient have occurred. The agent application may present the identifiers for the healthcare facilities to a healthcare worker in the form of a list shown on a display. However, in certain cases, the list may be long and difficult for the healthcare worker to read. Additionally, it may be challenging for the healthcare worker to visualize locations of the healthcare facilities, especially when the healthcare worker is not familiar with the locations of the healthcare facilities. Moreover, in order to display information about a clinical event that occurred at a healthcare facility in the list, the agent application must receive a selection of an identifier for the healthcare facility in the list. Navigating between multiple clinical events in such a fashion can place a strain on computing resources of a computing device executing the agent application and can be burdensome on the healthcare worker.

SUMMARY

The following is a brief summary of subject matter that is described in greater detail herein. This summary is not intended to be limiting as to the scope of the claims.

Various technologies pertaining to displaying locations of clinical events undergone by patients is disclosed herein. With more specificity, an agent application is described herein that displays locations of clinical events undergone by a patient alongside information about the clinical events. The agent application enables a user (i.e., a healthcare worker) of the agent application to visualize locations of the clinical events undergone by a patient so that the healthcare worker may more readily identify an undesirable pattern of behavior of the patient. Additionally, the agent application helps the healthcare worker to recommend healthcare facilities to patients. For instance, if the patient frequently visits healthcare facilities in a particular geographic area that is displayed by the agent application and the healthcare worker needs to make a referral, the healthcare worker may refer the patient to a healthcare facility in the geographic area.

In operation, responsive to receiving an identifier for a patient, an agent application executing on a computing device identifies one or more patient health records for the patient based upon the identifier for the patient. In an example, the agent application identifies a first patient health record for the patient and a second patient health record for the patient based upon the identifier for the patient. The first patient health record comprises an identifier for a first healthcare facility at which a first clinical event of the patient occurred and information about the first clinical event. The second patient health record comprises an identifier for a second healthcare facility at which a second clinical event of the patient occurred and information about the second clinical event. In an example, the first patient health record may have been generated by a first electronic health records (EHR) application and the second patient health record may have been generated by a second EHR application. In an embodiment, the agent application may identify the first patient health record and the second patient health record based upon dates included in the first patient health record and the second patient health record falling within a time range.

The agent application transmits the identifier for the first healthcare facility and the identifier for the second healthcare facility to a mapping computing system. Based upon the identifier for the first healthcare facility and the identifier for the second healthcare facility, the mapping computing system retrieves a map of an area that encompasses both the first healthcare facility and the second healthcare facility. The map includes a first marker that marks a location of the first healthcare facility on the map and a second marker that marks a location of the second healthcare facility on the map. The mapping computing system then transmits the map to the agent application.

Responsive to receiving the map from the mapping computing system, the agent application causes a first graphical indicator to be included in the map proximate to the first marker and a second graphical indicator to be included in the map proximate to the second marker. The first graphical indicator includes the identifier for the first healthcare facility and at least a portion of the information about the first clinical event. The second graphical indicator includes the identifier for the second healthcare facility and at least a portion of the information about the second clinical event. The agent application then causes the map to be displayed on a display. For instance, the agent application may cause the map to be displayed within a graphical user interface (GUI) for the agent application, the GUI for the agent application displayed concurrently with a GUI for an EHR that is also executing on the computing device. The first graphical indicator and the second graphical indicator may be presented in different manners (e.g., different colors, different shapes, etc.) in order to convey information about first clinical event and/or the second clinical event.

The above-described technologies present various advantages over conventional EHR applications and/or agent applications. First, unlike conventional EHR applications and/or agent applications, the above-described technologies enable information about a clinical event undergone by a patient to be displayed on a map that shows a location of a healthcare facility at which the clinical event occurred. Second, by displaying the information about the clinical event within the map, a healthcare worker examining the map can more readily ascertain undesirable patient behaviors (e.g., doctor shopping) based upon an examination of the map.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
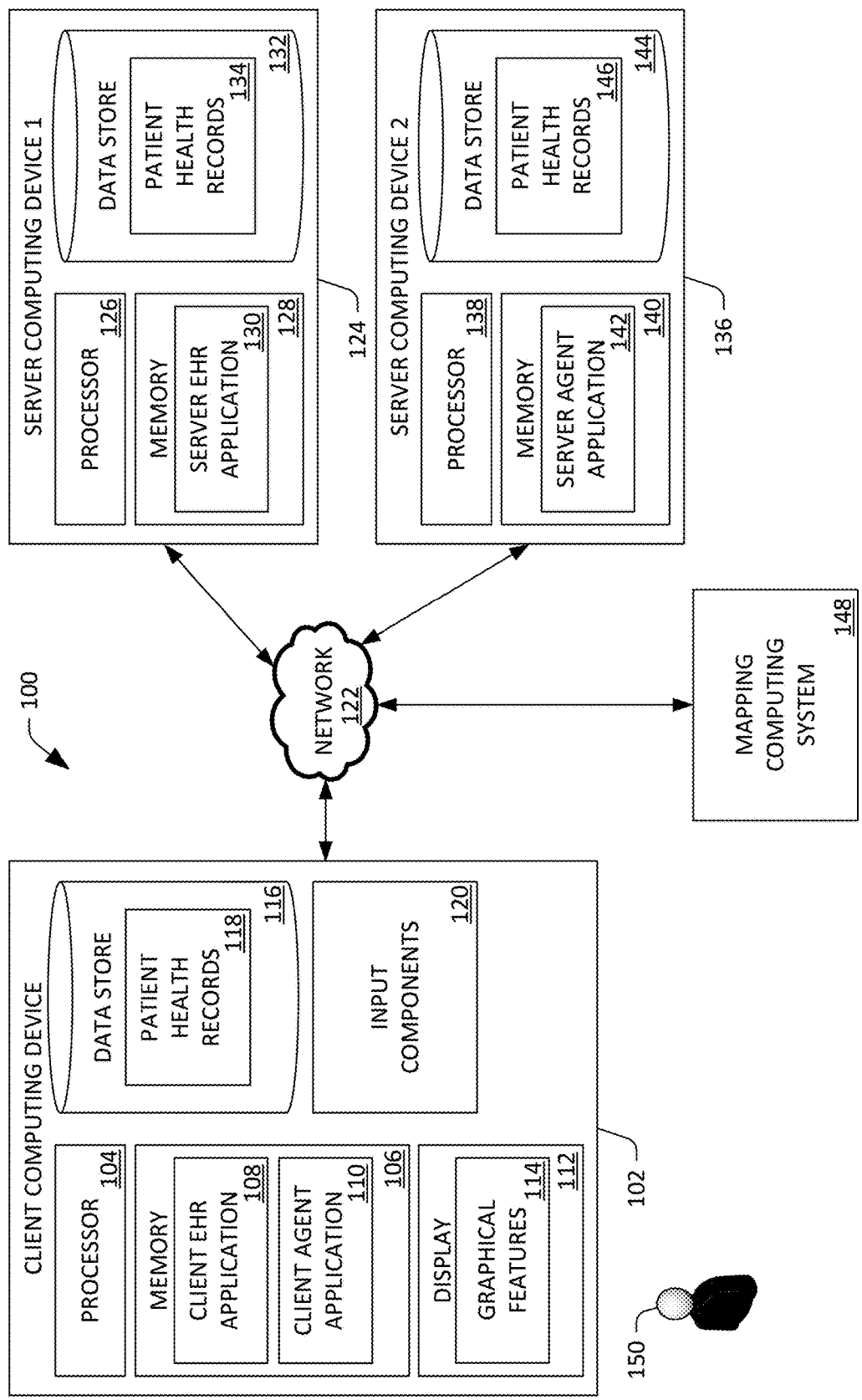
FIG. 1 is a functional block diagram of an exemplary computing system that facilitates displaying locations of clinical events undergone by patients.

Various technologies pertaining to displaying locations of clinical events undergone by patients are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details.

In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component," "application," and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary computing system 100 that facilitates displaying locations of clinical events undergone by patients is illustrated. The computing system 100 includes a client computing device 102 that is operated by a user 150 (e.g., a healthcare worker). In an example, the client computing device 102 may be a desktop computing device, a laptop computing device, a tablet computing device, a smartphone, or a wearable computing device, such as a smartwatch.

The client computing device 102 comprises a processor 104 and memory 106, wherein the memory 106 has a client electronic health records (EHR) application 108 and a client agent application 110 loaded therein. In general, the client EHR application 108 (when executed by the processor 104) is configured to communicate with a server EHR application in order to perform programmatic tasks related to patients in a healthcare facility. As will be described in greater detail below, the client agent application 110 (when executed by the processor 104) is configured to retrieve and display patient health records (or portions thereof) for a patient on a map. The patient health records are aggregated from a plurality of electronic sources. In an example, the plurality of electronic sources may include different EHR applications, different Health Information Exchanges (HIEs), and/or other third-party applications. The client computing device 102 may execute the client EHR application 108 and the client agent application 110 concurrently. For instance, the client computing device 102 may present a graphical user interface (GUI) for the client EHR application 108 concurrently with a GUI for the client agent application 110. In an embodiment, the client computing device 102 may present the GUI for the client agent application 110 as an overlay to the GUI for the client EHR application 108.

The client computing device 102 further comprises a display 112, whereupon graphical features 114 may be presented thereon. For instance, a GUI for the client EHR application 108 and/or a GUI for the client agent application 110 may be displayed on the display 112 as part of the graphical features 114. In an embodiment, the display 112 may be a touchscreen display.

The client computing device 102 further comprises a data store 116. The data store 116 may store patient health records 118 for patients. The patient health records 118 may overlap in part or wholly with patient health records (described below) maintained by a server agent application (also described below).

The client computing device 102 additionally comprises input components 120 that enable the client computing device 102 to receive input from the user 150. In an example, the input components 120 may include a mouse, a keyboard, a touchscreen, a scroll wheel, a trackpad, a microphone, a camera, and/or a video camera.

The computing system 100 further comprises a first server computing device 124 that is in communication with the client computing device 102 by way of a network 122 (e.g., the Internet, intranet, etc.). The first server computing device 124 comprises a processor 126 and memory 128, wherein the memory 128 has a server EHR application 130 loaded therein. In general, the server EHR application 130 (when executed by the processor 126) is configured to communicate with the client EHR application 108 in order to perform a variety of programmatic tasks related to patient healthcare in a healthcare facility (e.g., patient intake, prescription generation, patient health record creation and maintenance, etc.). Thus, the server EHR application 130 and the client EHR application 108 form a distributed application with both server-side and client-side functionality, respectively, collectively referred to herein as "an EHR application."

The first server computing device 124 further comprises a data store 132 that stores patient health records 134 that are maintained by the server EHR application 130. The patient health records 134 may include electronic health records, prescription records, claims data, patient/disease registries, health surveys data, clinical trials data, etc.

The computing system 100 further comprises a second server computing device 136. The second server computing device 136 is in communication with the client computing device 102 by way of the network 122 (or another network). The second server computing device 136 may also be in communication with the first server computing device 124 by way of the network 122 (or another network).

The second server computing device 136 comprises a processor 138 and memory 140, wherein the memory 140 has a server agent application 142 loaded therein. In general, the server agent application 142 (when executed by the processor 138) is configured to retrieve patient health records from a plurality of electronic sources (as opposed to patient health records from a single electronic source, as with the server EHR application 130) and to provide the patient health records to the client agent application 110 for display on the display 112 as part of the graphical features 114. Thus, the server agent application 142 and the client agent application 110 form a distributed application with both server-side and client-side functionality, respectively, collectively referred to herein as "an agent application."

The second server computing device 136 further comprises a data store 144 that stores patient health records 146 for patients. The patient health records 146 may include electronic health records, prescription records, claims data, patient/disease registries, health surveys data, clinical trials data, etc. As noted above, the patient health records 146 are aggregated from a plurality of electronic sources (e.g., different EHR applications, different HIEs, etc.).

An exemplary patient health record for a patient in the patient health records 146 comprises an identifier for a healthcare facility at which a clinical event of the patient occurred and information about the clinical event. The identifier for the healthcare facility may be a name of the healthcare facility, a code for the healthcare facility, an address of the healthcare facility, etc. In an example, a clinical event may be being treated for an injury at a healthcare facility, being prescribed a medication at a healthcare facility, undergoing a procedure at a healthcare facility, being diagnosed with a medical condition at a healthcare facility, etc. As used herein, the term "clinical event" is meant to encompass an interaction of a patient with a healthcare worker at a healthcare facility for the purpose of providing care to the patient. The information about the clinical event may include a date and time at which the clinical event occurred, identifiers for one or more healthcare workers involved in the clinical event (i.e., healthcare workers that treated the patient), a type of the healthcare facility (e.g., inpatient facility, outpatient facility, emergency room facility, specialist facility, ambulatory facility, etc.) at which the clinical event occurred, notes taken by a healthcare worker during the clinical event, identifiers for one or more medications prescribed to the patient as part of the clinical events, problems of the patient (e.g. injuries) conveyed by the patient to the one or more healthcare worker during the clinical event, procedures undergone by the patient during the clinical event, laboratory orders for the patient generated as part of the clinical event, care plans for the patient generated or updated as part of the clinical event, identifiers for medical conditions of the patient diagnosed by the one or more healthcare workers during the clinical event, etc.

The computing system 100 additionally comprises a mapping computing system 148 that is in communication with the second server computing device 136 by way of the network 122 (or another network). In an embodiment, the mapping computing system 148 may also be in communication with the client computing device 102 by way of the network 122 (or another network). As will be described in greater detail, the mapping computing system 148 is configured to retrieve maps that show locations of healthcare facilities based upon identifiers for healthcare facilities.

Operation of the computing system 100 is now set forth. Subsequent to the user 150 being authenticated by the server agent application 142 based upon credentials for the user 150, the client agent application 110 receives an identifier for a patient as input from the user 150. The client agent application 110 transmits the identifier for the patient to the server agent application 142.

Responsive to receiving the identifier for the patient from the client agent application 110, the server agent application 142 identifies a patient health record for the patient based upon the identifier for the patient. More specifically, the server agent application 142 may execute a search over the patient health records 146 based upon the identifier for the patient. The search produces search results, wherein the search results include the patient health record for the patient.

The patient health record comprises an identifier for a healthcare facility at which a clinical event of the patient occurred and information about the clinical event. In an example, the clinical event may be receiving treatment at the healthcare facility (e.g., receiving treatment for an injury), being prescribed a medication by a healthcare worker at the healthcare facility, undergoing a procedure at the healthcare facility, having a laboratory test ordered at the healthcare facility, etc. In an example, when the clinical event is being prescribed a medication by a healthcare worker, the information about the clinical event may include an identifier for the medication that was prescribed, an identifier for the healthcare worker that prescribed the medication, a date and time at which the medication was prescribed, etc. In another example, when the clinical event is undergoing a procedure at the healthcare facility, the information about the clinical event may include an identifier for the procedure, results of the procedure, a date and time of the procedure, etc.

Subsequent to identifying the patient health record, the server agent application 142 transmits the identifier for the healthcare facility (that is comprised by the patient health record) to the mapping computing system 148. For instance, the server agent application 142 may transmit the identifier for the healthcare facility to the mapping computing system 148 via an application programming interface (API) call to the mapping computing system 148. Responsive to receiving the identifier for the healthcare facility, the mapping computing system 148 retrieves a map of an area encompassing the healthcare facility based upon the identifier for the healthcare facility. The map includes a marker that marks a location of the healthcare facility on the map. The mapping computing system 148 transmits the map to the server agent application 142.

In an embodiment, the server agent application 142 may identify the patient health record for the patient further based upon a date range and a date included in the information about the clinical event (i.e., a date upon which the clinical event occurred). For instance, the server agent application 142 may receive a date range from the client agent application 110 (as input from the user 150). The date range may also be predetermined (e.g., a 3-month date range, a 6-month date range). When a date included in the patient health record falls within the date range, the server agent application 142 may identify the patient health record as being relevant and as such the server agent application 142 may transmit the identifier for the healthcare facility to the mapping computing system 148. Alternatively, when the date included in the patient health record does not fall within the date range, the server agent application 142 may identify the patient health record as not being relevant, and as such the server agent application 142 may fail to transmit the identifier for the healthcare facility to the mapping computing system 148.

Responsive to receiving the map from the mapping computing system 148, the server agent application 142 causes a graphical indicator to be included in the map proximate to the marker. More specifically, the server agent application 142 may read metadata embedded in the map to determine the location of the marker, and the server agent application 142 may cause the graphical indicator to be included in the map responsive to determining the location of the marker.

The graphical indicator included in the map includes the identifier for the healthcare facility (or another identifier for the healthcare facility) and at least a portion of the information about the clinical event comprised by the patient health record. The server agent application 142 then causes the map to be displayed on the display 112 as part of the graphical features 114. More specifically, the server agent application 142 transmits the map to the client agent application 110, whereupon the client agent application 110 displays the map within a GUI for the client agent application 110 that is displayed on the display 112 as part of the graphical features 114.

The graphical indicator and/or the marker may be selectable within the map. Responsive to receiving a selection (e.g., a mouse-click) of the graphical indicator and/or the marker, the client agent application 110 may cause the patient health record (that corresponds to the graphical indicator and the marker) to be displayed on the display 112. More specifically, responsive to receiving the selection, the client agent application 110 may transmit an identifier for the patient health record to the server agent application 142. The server agent application 142 retrieves the patient health record for the patient based upon the identifier for the patient health record. The server agent application 142 then transmits the patient health record to the client agent application 110. The client agent application 110 presents the patient health record on the display 112 (e.g., within the GUI for the client agent application 110). Alternatively, if the patient health record is stored in the memory 106 or the data store 116, the client agent application 110 can display the patient health record on displays responsive to receiving the selection.

It is to be understood that the server agent application 142 may identify more than one patient health record for the patient based upon the identifier for the patient. Likewise, the area of the map retrieved by the mapping computing system 148 may encompass more than one healthcare facility. In an example, the server agent application 142 identifies a second patient health record for the patient based upon the identifier for the patient. The second patient health record comprises an identifier for a second healthcare facility at which a second clinical event of the patient occurred and information about the second clinical event. The second patient health record may be generated by a different electronic source than that of the patient health record. For instance, a first EHR application may generate the patient health record, whereas a second EHR application may generate the second patient health record.

The server agent application 142 may transmit the identifier for the second healthcare facility to the mapping computing system 148 concurrently with transmitting the identifier for the healthcare facility to the mapping computing system 148. The map retrieved by mapping computing system thus encompasses both the location of the healthcare facility and a location of the second healthcare facility. Moreover, the map includes the marker that marks the location of the healthcare facility on the map, as well as a second marker that marks the location of the second healthcare facility on the map. Responsive to receiving the map from the mapping computing system 148, the server agent application 142 causes a second graphical indicator (in addition to the graphical indicator) to be included in the map. The second graphical indicator includes the identifier for the second healthcare facility and at least a portion of the information about the second clinical event. As a result, the map displayed on the display 112 includes the marker, the graphical indicator, the second marker, and the second graphical indicator. In an example, the graphical indicator may include a first date on which the clinical event occurred and the second graphical indicator may include a second date on which the second clinical event occurred. In another example, the graphical indicator may include an identifier for a medication prescribed to the patient as part of the clinical event and the second graphical indicator may include an identifier for a second medication prescribed to the patient as part of the second clinical event. The healthcare worker 150 may then view the map in order to ascertain undesirable patterns of behavior by the patient. Additionally, the healthcare worker 150 may view the map in order to recommend healthcare facilities to patients at which the patient can undergo clinical events. For instance, if the patient frequently visits healthcare facilities in a particular geographic area represented by the map and the healthcare worker 150 needs to make a referral, the healthcare worker 150 may refer the patient to a healthcare facility in the geographic area represented by the map.

In an embodiment, graphical indicators included in the map may be displayed in different colors and/or shapes to highlight certain aspects of clinical events corresponding to the graphical indicators. In an example, the client agent application 110 may present the graphical indicator in a first color (e.g., red) to indicate that the clinical event corresponding to the graphical indicator occurred more recently (compared to the current date) than the second clinical event corresponding to the second graphical indicator, whereas the client agent application 110 may present the second graphical indicator in a second color (e.g., blue) to indicate that the second clinical event corresponding to the second graphical indicator occurred more distantly (compared to the current date) than the clinical event corresponding to the graphical indicator.

In another example, graphical indicators included in the map may be displayed as different shapes (or colors) to indicate types of clinical events. For instance, the client agent application 110 may present the graphical indicator as a first shape (e.g., a square) to indicate that the clinical event is a first type of clinical event, the first shape being assigned to the first type of clinical event, whereas the client agent application 110 may present the second graphical indicator as a second shape (e.g., a circle) to indicate that the second clinical event is a second type of clinical event, the second shape being assigned to the second type of clinical event.

In yet another example, the graphical indicators included in the map may be displayed as different shapes (or colors) to indicate different types of healthcare facilities at which clinical events corresponding to the graphical indicators occurred. For instance, the client agent application 110 may present the graphical indicator as a first shape to indicate that the clinical event occurred at a first type of healthcare facility, the first shape being assigned to the first type of healthcare facility, whereas the client agent application 110 may present the second graphical indicator as a second shape to indicate that the second clinical event occurred at a second type of healthcare facility, the second shape being assigned to the second type of healthcare facility.

In an embodiment, the server agent application 142 identifies a plurality of patient health records for the patient corresponding to a plurality of clinical events of the patient that have occurred at a plurality of healthcare facilities. The map retrieved by the mapping computing system 148 thus comprises a plurality of graphical indicators that each correspond to a different clinical event. In the embodiment, the server agent application 142 determines a number of times in which a designated clinical event (e.g., being prescribed a particular medication) is repeated throughout the plurality of patient health records. When the number of times exceeds a threshold value, the server agent application 142 may cause an alert to be transmitted to the client agent application 110, the alert indicating that the number of times that the designated clinical event has occurred has exceeded the threshold value. The client agent application 110 may present the alert within the GUI for the client agent application 110.

Figure 2:
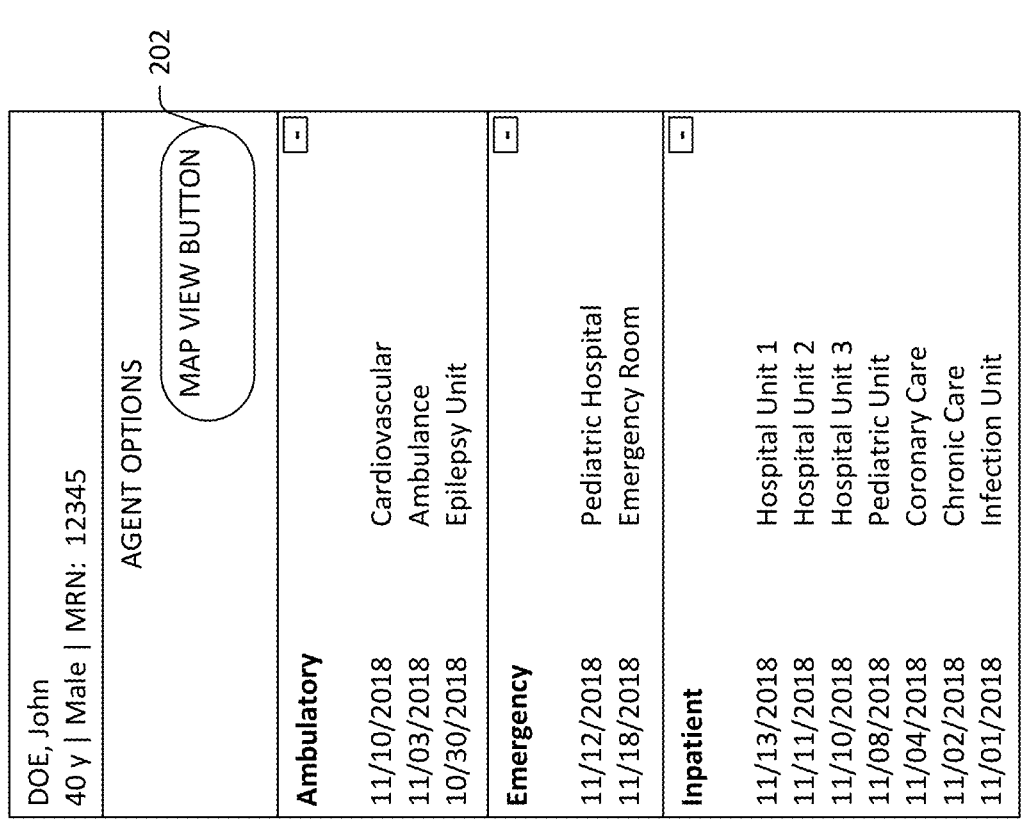
FIG. 2 is an exemplary graphical user interface (GUI) for a client agent application.

Referring now to FIG. 2, an exemplary GUI 200 for the client agent application 110 that can be presented on the display 112 as part of the graphical features 114 is depicted. The GUI 200 for the client agent application 110 may be presented on the display 112 concurrently with a GUI for the client EHR application 108. As shown in FIG. 2, the GUI 200 includes information about a patient (e.g., an identifier for the patient, a gender of the patient, an age of the patient, a medical record number of the patient, etc.). The GUI 200 also displays identifiers for healthcare facilities (e.g., Hospital Unit 1, Emergency Room, etc.) at which clinical events for the patient have occurred. The GUI 200 additionally includes a map view button 202. When the GUI 200 for the client agent application 110 receives a selection of the map view button 202, the client agent application 110 may cause a map to be presented on the display 112 as part of the graphical features 114. More specifically, responsive to receiving the selection of the map view button 202, the client agent application 110 may transmit the identifier for the patient to the server agent application 142 (as described above), and the server agent application 142 may cause the client application 110 to receive and display the map.

Figure 3:
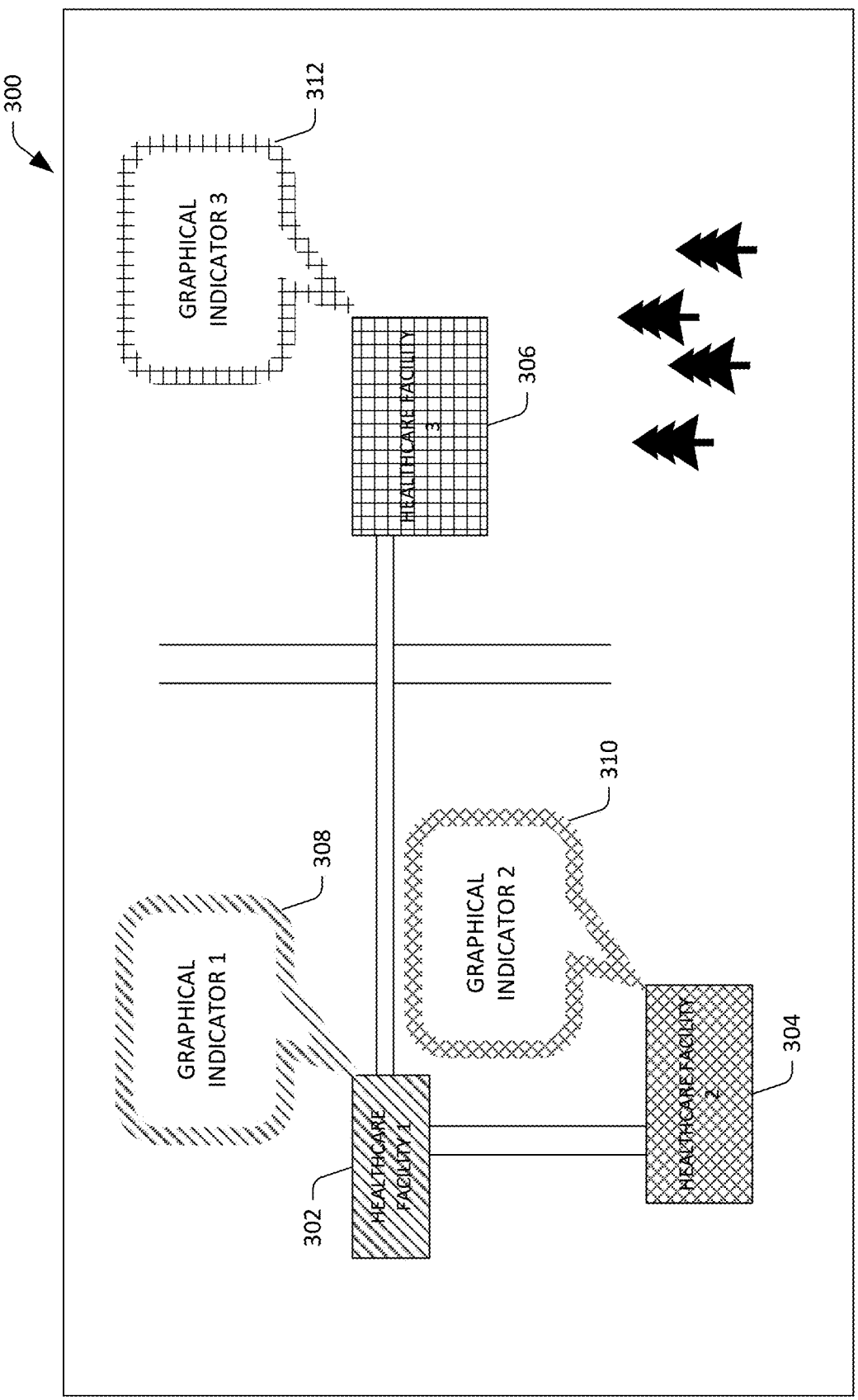
FIG. 3 is a depiction of an exemplary map presented by a client agent application that depicts locations of clinical events undergone by patients.

Turning now to FIG. 3, an exemplary map 300 that depicts locations of clinical events undergone by a patient is illustrated. The client agent application 110 may present the map 300 on the display 112 within a GUI for the client agent application 110 responsive to the client agent application 110 receiving a selection of the map view button 202 displayed within the GUI 200.

In the example shown in FIG. 3, the server agent application 142 has identified three patient health records corresponding to three clinical events that the patient has undergone. As such, the map 300 includes a first marker 302 corresponding to a first healthcare facility at which a first clinical event of the patient occurred, a second marker 304 corresponding to a second healthcare facility at which a second clinical event of the patient occurred, and a third marker 306 corresponding to a third healthcare facility at which a third clinical event of the patient occurred. The map 300 further includes a first graphical indicator 308 that displays information about the first clinical event, a second graphical indicator 310 that displays information about the second clinical event, and a third graphical indicator 312 that displays information about the third clinical event. The dates upon which the first clinical event, the second clinical event, and the third clinical event occurred may be indicated by a color gradient displayed within the first graphical indicator 308, the second graphical indicator 310, and the third graphical indicator 312 (illustrated in FIG. 3 through different cross-hatching patterns). Additionally, or alternatively, the color gradient may also be displayed within the first marker 302, the second marker 304, and the third marker 304. The map 300 may also include additional geographical features (e.g., roads, trees, non-healthcare related buildings, etc.) located around the first healthcare facility, the second healthcare facility, and the third healthcare facility.

Figure 4:
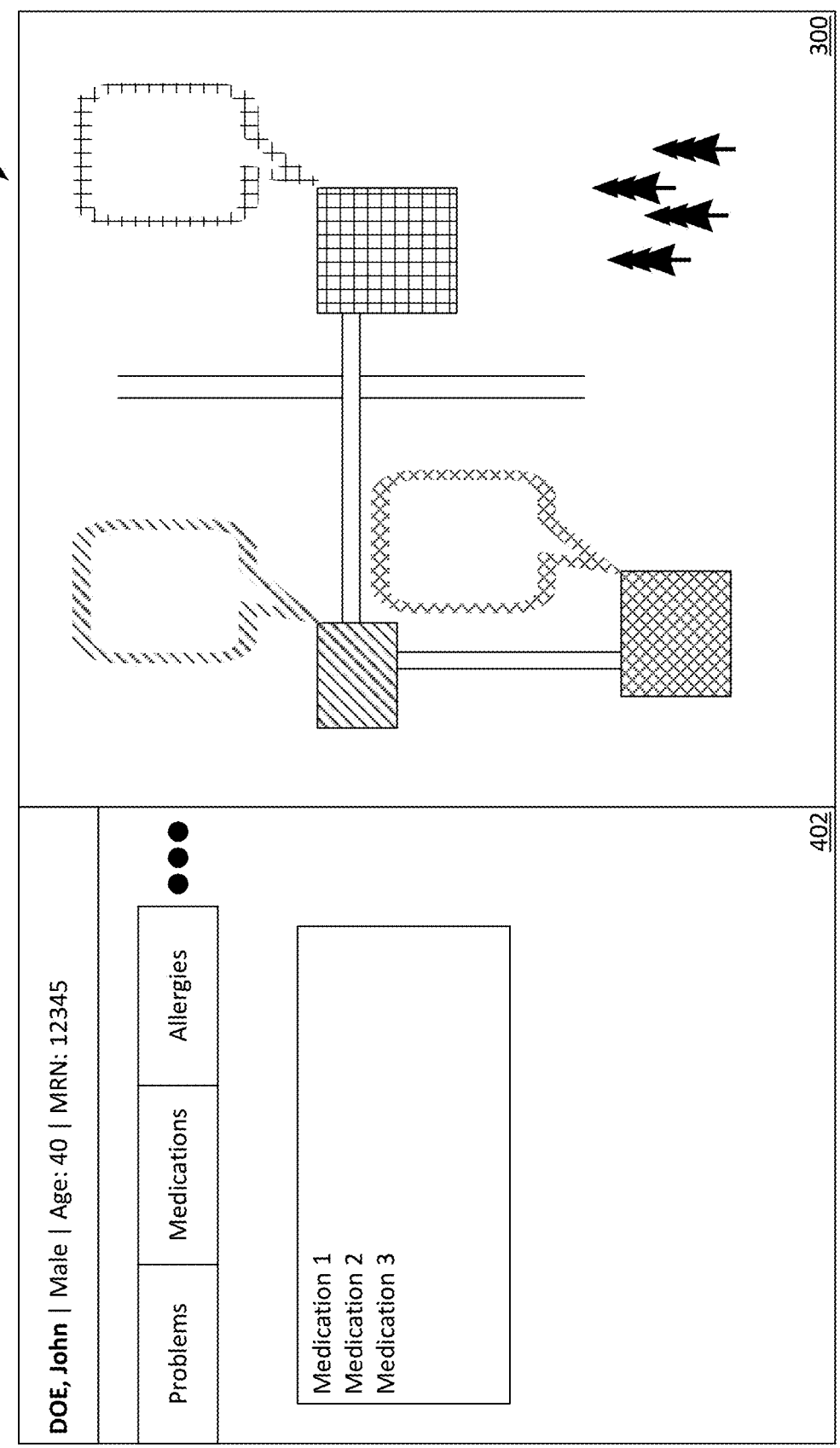
FIG. 4 is a view of a GUI for a client agent application and a GUI for a client electronic health records application being displayed simultaneously on a display.

Referring now to FIG. 4, a view 400 shown on the display 112 of the client computing device 102 is depicted. As shown in FIG. 4, the view 400 includes the map 300 (described above), which is displayed within a GUI for the client agent application 110. The view 400 also includes a GUI 402 for the client EHR application 108. As shown in FIG. 4, the GUI 402 for the client EHR application 108 displays clinical data for the patient (e.g., information pertaining to medications of the patient). Thus, it is to be understood that the GUI for the client agent application 110 (which includes the map 300) and the GUI 402 for the client EHR application 108 may be presented simultaneously on the display 112 as part of the graphical features 114.

Although the above-described functionality has been described as being primarily performed by the server agent application 142, other possibilities are contemplated. For instance, in an embodiment, the client agent application 110 may perform some or all of the functionality described above as being performed by the server agent application 142. For example, the client agent application 110 may transmit the identifier for the patient to the server agent application 142, the server agent application 142 may identify the patient health record for the patient based upon the identifier for the patient, and the server agent application 142 may transmit the patient health record to the client agent application 110. The client agent application 110 may then transmit the identifier for the healthcare facility to the mapping computing system 148, and the mapping computing system 148 may retrieve the map as described above based upon the identifier for the healthcare facility. Responsive to receiving the map from the mapping computing system 148, the client agent application 110 may cause the graphical indicator to be included in the map proximate to the marker included in the map. The client agent application 110 may then display the map on the display 112 as part of the graphical features 114.

Although the graphical indicators described above have been described as being included in the map generated by the server agent application 142, other possibilities are contemplated. For instance, in an embodiment, the server agent application 142 may transmit data along with the map that causes an overlay to be presented on the map, the overlay including the graphical indicators described above.

Although the map described above has been described as being retrieved by the mapping computing system 148, other possibilities are contemplated. For instance, in an embodiment, some or all of the functionality of the mapping computing system 148 may be incorporated into the agent application. In the embodiment, the agent application may have access to a set of maps. The agent application may retrieve the map (in the set of maps) based upon one or more identifiers for healthcare facilities.

Figure 5:
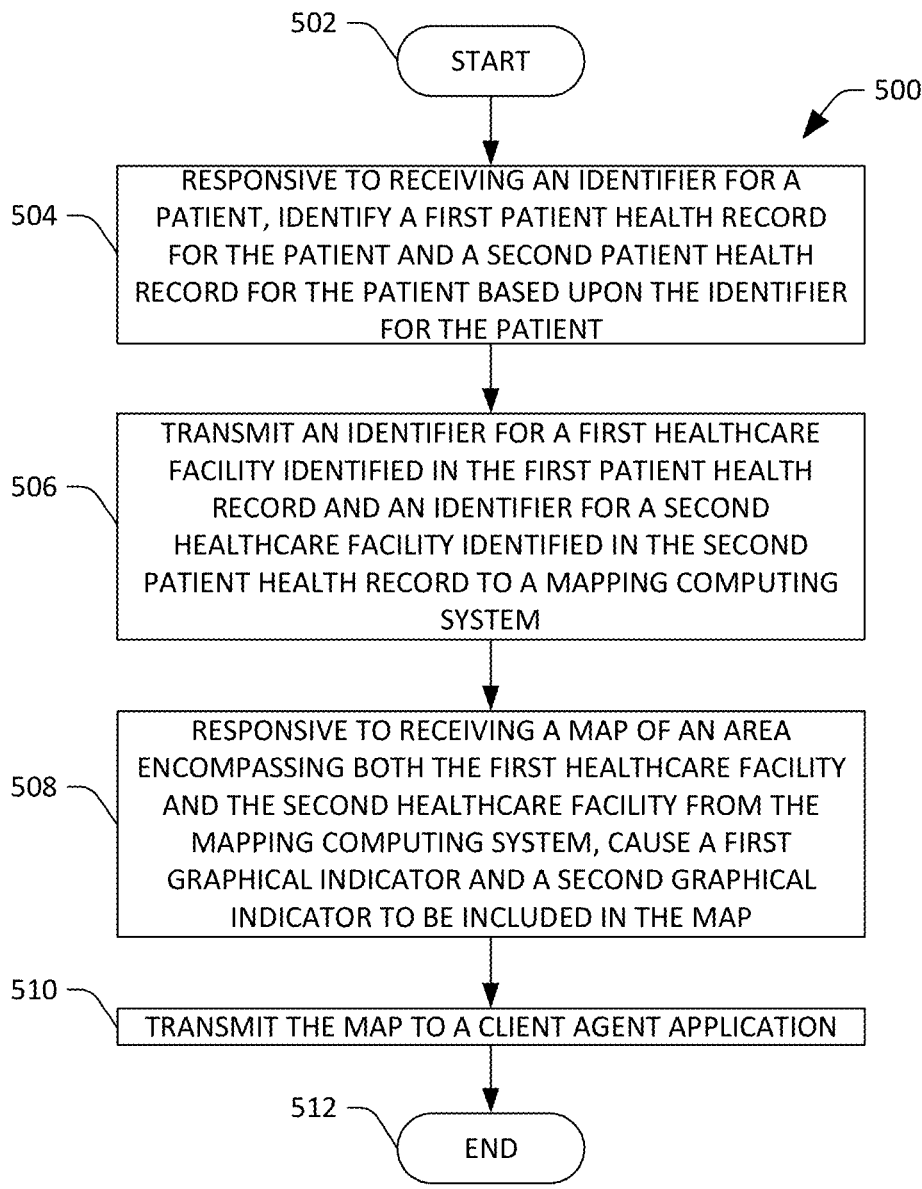
FIG. 5 is a flow diagram that illustrates an exemplary methodology performed by a server agent application that facilitates displaying locations of clinical events undergone by patients.
Figure 6:
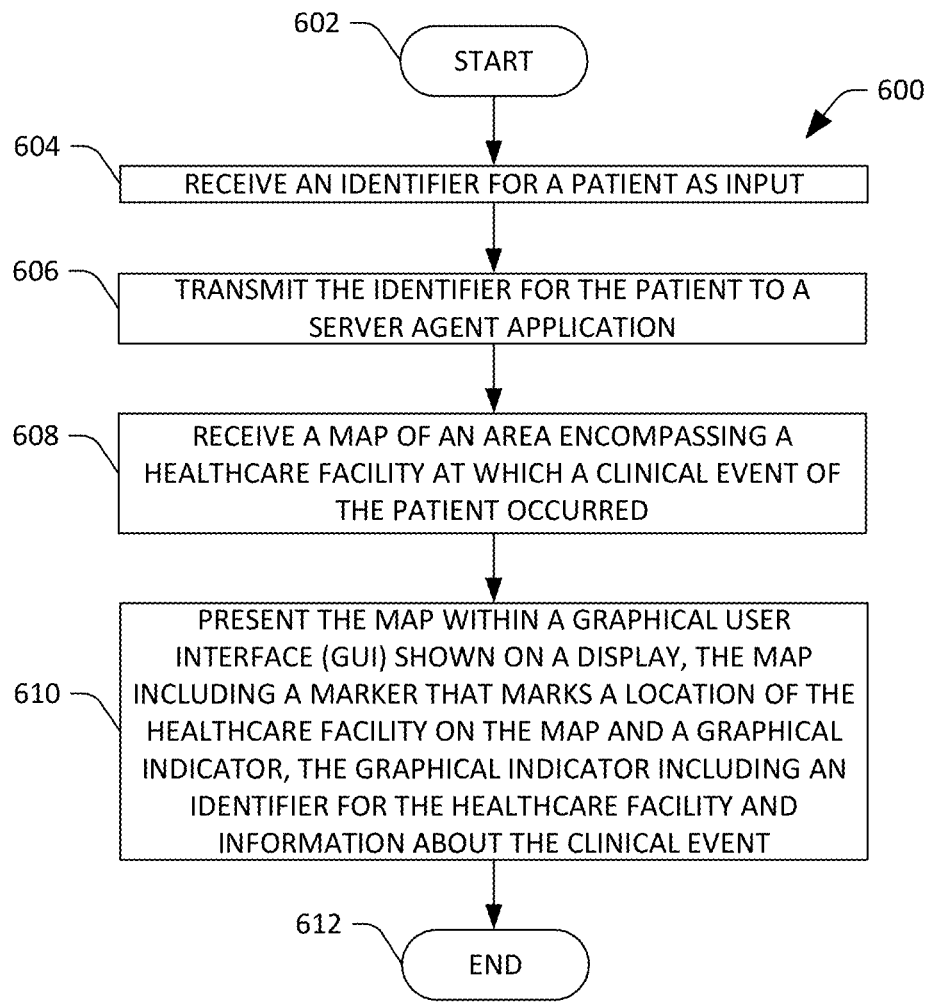
FIG. 6 is a flow diagram that illustrates an exemplary methodology executed by a client agent application that facilitates displaying locations of clinical events undergone by patients.

FIGS. 5 and 6 illustrate exemplary methodologies relating to displaying locations of clinical events undergone by patients. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 5, a methodology 500 performed by a server agent application executing on a server computing device that facilitates displaying locations of clinical events undergone by patients is illustrated. The methodology 500 begins at 502, and at 504, responsive to receiving an identifier for a patient from a client agent application executing on a client computing device that is in network communication with the server computing device, the server agent application identifies a first patient health record for the patient and a second patient health record for the patient based upon the identifier for the patient. The first patient health record comprises an identifier for a first healthcare facility at which a first clinical event of the patient occurred and information about the first clinical event. The second patient health record comprises an identifier for a second healthcare facility at which a second clinical event of the patient occurred and information about the second clinical event.

At 506, the server agent application transmits the identifier for the first healthcare facility and the identifier for the second healthcare facility to a mapping computing system that is in network communication with the server computing device. The mapping computing system retrieves a map of an area encompassing both the first healthcare facility and the second healthcare facility based upon the identifier for the first healthcare facility and the identifier for the second healthcare facility. The map includes a first marker that marks a location of the first healthcare facility on the map and a second marker that marks a location of the second healthcare facility on the map. The mapping computing system transmits the map to the server agent application.

At 508, responsive to receiving the map from the mapping computing system, the server agent application causes a first graphical indicator to be included in the map proximate to the first marker and a second graphical indicator to be included in the map proximate to the second marker. The first graphical indicator includes the identifier for the first healthcare facility and the information about the first clinical event (or a portion thereof). The second graphical indicator includes the identifier for the second healthcare facility and the information about the second clinical event (or a portion thereof). At 510, the server agent application transmits the map to the client agent application. The client agent application presents the map within a GUI for the client agent application shown on a display. The GUI for the client agent application is presented concurrently on the display with a GUI for a client EHR application executing on the client computing device. The methodology 500 concludes at 512.

Turning now to FIG. 6, a methodology 600 executed by a client agent application executing on a client computing device that facilitates displaying locations of clinical events undergone by patients is illustrated. The methodology 600 begins at 602, and at 604, the client agent application receives an identifier for a patient as input from a user of the client agent application. At 606, the client agent application transmits the identifier for the patient to a server agent application executing on a server computing device that is in network communication with the client computing device. The server agent application retrieves a patient health record for the patient based upon the identifier for the patient, the patient health record comprising an identifier for a healthcare facility at which a clinical event of the patient occurred and information about the clinical event. The server agent application also communicates with a mapping computing system in order to obtain a map of an area encompassing the healthcare facility.

At 608, the client agent application receives the map from the server agent application. At 610, the client agent application presents the map within a GUI for the client agent application shown a display of the client computing device. The map includes a marker that marks a location of the healthcare facility on the map and a graphical indicator that is located proximate to the marker in the map. The graphical indicator includes the identifier for the healthcare facility and the information about the clinical event (or a portion thereof). The methodology 600 concludes at 612.

Figure 7:
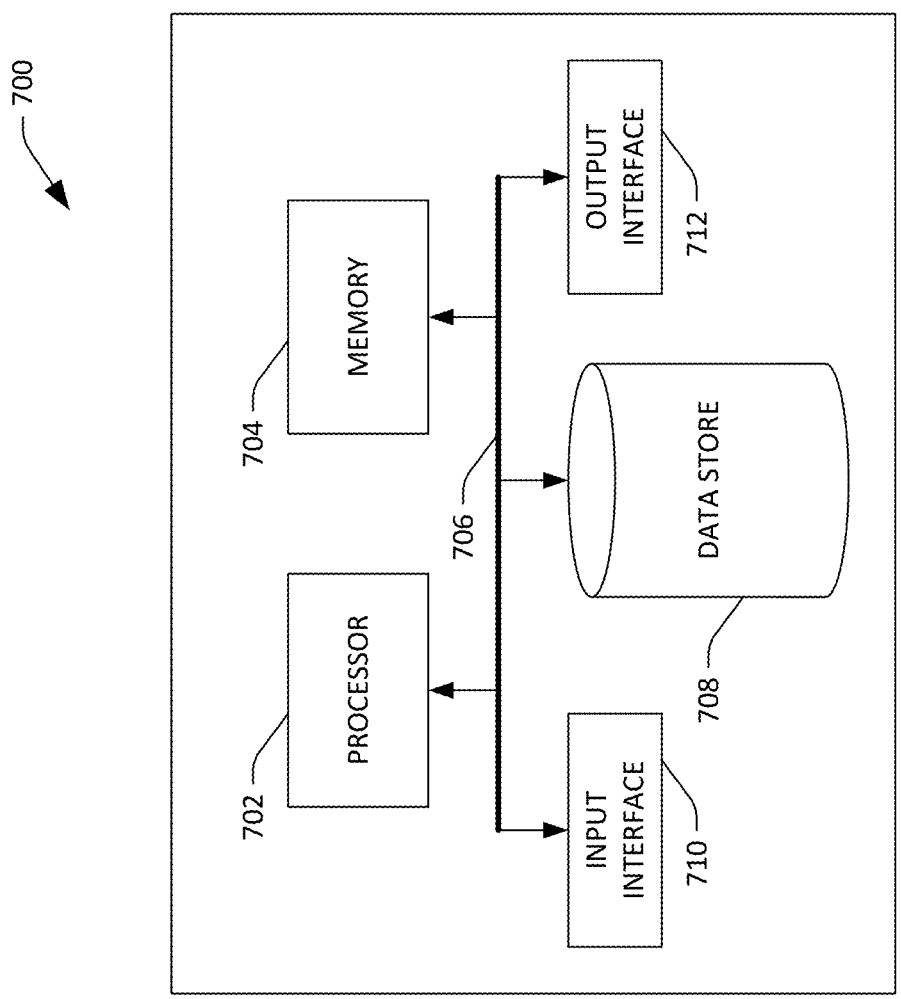
FIG. 7 is an exemplary computing system.

Referring now to FIG. 7, a high-level illustration of an exemplary computing device 700 that can be used in accordance with the systems and methodologies disclosed herein is illustrated. For instance, the computing device 700 may be used in a system that displays locations of clinical events undergone by a patient on a map. By way of another example, the computing device 700 can be used in a system that retrieves patient health records for a patient from a plurality of electronic sources. The computing device 700 includes at least one processor 702 that executes instructions that are stored in a memory 704. The instructions may be, for instance, instructions for implementing functionality described as being carried out by one or more components discussed above or instructions for implementing one or more of the methods described above. The processor 702 may access the memory 704 by way of a system bus 706. In addition to storing executable instructions, the memory 704 may also store patient health records, maps, etc.

The computing device 700 additionally includes a data store 708 that is accessible by the processor 702 by way of the system bus 706. The data store 708 may include executable instructions, patient health records, maps, etc. The computing device 700 also includes an input interface 710 that allows external devices to communicate with the computing device 700. For instance, the input interface 710 may be used to receive instructions from an external computer device, from a user, etc. The computing device 700 also includes an output interface 712 that interfaces the computing device 700 with one or more external devices. For example, the computing device 700 may display text, images, etc. by way of the output interface 712.

It is contemplated that the external devices that communicate with the computing device 700 via the input interface 710 and the output interface 712 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 700 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 700 may be a distributed system. Thus, for instance, several devices may be in communication by way of a network connection and may collectively perform tasks described as being performed by the computing device 700.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A server computing device that is in communication with a client computing device by way of a network connection between the server computing device and the client computing device, the server computing device; comprising:
  a processor; and
  memory storing a server agent application that, when executed by the processor, causes the processor to perform acts comprising:
    receiving, from a client agent application that is executing on a client computing device, an identifier for a patient, wherein the client computing device executes a client electronic health records application (EHR), wherein a graphical user interface (GUI) of the client agent application is displayed concurrently on a display of the client computing device with a GUI of the client EHR, and further wherein the identifier for the patient is received from the client agent application due to the GUI of the client EHR displaying the identifier for the patient on the display of the client computing device;
    responsive to receiving the identifier for a patient and based upon the identifier for the patient, identifying a first patient health record for the patient and a second patient health record for the patient from a computer-readable data store that comprises health records for patients, wherein the first patient health record comprises:
      an identifier for a first healthcare facility at which a first clinical event of the patient occurred; and
      information about the first clinical event;
    wherein the second patient health record comprises:
      an identifier for a second healthcare facility at which a second clinical event of the patient occurred; and
      information about the second clinical events;
      transmitting the identifier for the first healthcare facility and the identifier for the second healthcare facility to a mapping computing system;

receiving, from the mapping computing system, a map of an area encompassing both the first healthcare facility and the second healthcare facility, wherein the map is retrieved by the mapping computing system based upon the identifier for the first healthcare facility and the identifier for the second healthcare facility, wherein the map includes a first marker that marks a location of the first healthcare facility on the map and a second marker that marks a location of the second healthcare facility on the map;

responsive to receiving the map from the mapping computing system, updating the map to include:

a first graphical indicator positioned to visually correspond to the first marker; and a second graphical indicator positioned to visually correspond to the second marker, wherein the first graphical indicator includes the identifier for the first healthcare facility and at least a portion of the information about the first clinical event, and further wherein the second graphical indicator includes the identifier for the second healthcare facility and at least a portion of the information about the second clinical event; and causing the updated map to be displayed within the GUI of the client agent application on the display of the client computing device such that the map is displayed concurrently with the GUI for the client EHR application.

2. The computing device of claim 1, wherein causing the updated map to be displayed on the display of the client computing device comprises transmitting the map to the client agent application.

3. The computing device of claim 2, wherein the first patient health record was generated by a first EHR application, wherein the second patient health record was generated by a second EHR application.

4. The computing device of claim 1, wherein the first clinical event is treatment for a first injury of the patient at the first healthcare facility, wherein the second clinical event is treatment for a second injury of the patient at the second healthcare facility.

5. The computing device of claim 1, wherein the at least a portion of the information about the first clinical event included in the first graphical indicator further includes a first date on which the first clinical event occurred, wherein the at least a portion of the information about the second clinical event included in the second graphical indictor further includes a second date on which the second clinical event occurred.

6. The computing device of claim 1, wherein the first graphical indicator is presented in a first color on the map, wherein the second graphical indicator is presented in a second color on the map, wherein the first color indicates that the first clinical event occurred prior to the second clinical event, and further wherein the second color indicates that the second clinical event occurred subsequent to the first clinical event.

7. The computing device of claim 1, wherein the at least a portion of the information about the first clinical event included in the first graphical indicator comprises an identifier for a first medication prescribed to the patient at the first healthcare facility as part of the first clinical event, wherein the at least a portion of the information about the second clinical event included in the second graphical indicator comprises an identifier for a second medication prescribed to the patient at the second healthcare facility as part of the second clinical event.

8. The computing device of claim 1, wherein the information about the first clinical event further includes a first date on which the first clinical event occurred, wherein the information about the second clinical event further includes a second date on which the second clinical event occurred, the acts further comprising:

prior to transmitting the identifier for the first healthcare facility and the identifier for the second healthcare facility to the mapping computing system, receiving a date range from the client agent application, wherein identifying the first patient health record and the second patient health record is further based upon the first date and the second date falling within the date range.

9. The computing device of claim 1, wherein the first patient health record further comprises a type of the first healthcare facility, wherein the first graphical indicator identifies the type of the first healthcare facility, wherein the second patient health record further comprises a type of the second healthcare facility, wherein the second graphical indicator identifies the type of the second healthcare facility.

10. The computing device of claim 1, wherein the identifier for the first healthcare facility comprises an address of the first healthcare facility, wherein the identifier for the second healthcare facility comprises an address of the second healthcare facility.

11. A method executed by a processor of a server computing device as the server computing device executes a server agent application, the method comprising:

receiving an identifier for a patient from a client agent application that is executing on a client computing device, wherein the client computing device executes a client electronic health records application (EHR), wherein a graphical user interface (GUI) of the client agent application is displayed concurrently on a display of the client computing device with a GUI of the client EHR, and further wherein the identifier for the patient is received from the client agent application due to the GUI of the client EHR displaying the identifier for the patient on the display of the client computing device;

responsive to receiving the identifier for the patient from the client agent application and based upon the identifier for the patient, identifying a first patient health record for the patient and a second patient health record for the patient from a computer-readable data store, wherein the first patient health record comprises:

an identifier for a first healthcare facility at which a first clinical event of the patient occurred; and information about the first clinical event, wherein the second patient health record comprises:

an identifier for a second healthcare facility at which a second clinical event of the patient occurred; and information about the second clinical event;

transmitting a request for a map to a mapping computing system, wherein the request for the map comprises the identifier for the first healthcare facility and the identifier for the second healthcare facility;

receiving the map from the mapping computing system, wherein the map represents an area encompassing both the first healthcare facility and the second healthcare facility, wherein the map includes a first marker that marks a location of the first healthcare facility on the map, wherein the map;

responsive to receiving the map from the mapping computing system, updating the map to include a first graphical indicator that visually corresponds to the first marker and a second graphical indicator that visually corresponds to the second marker, the first graphical indicator including the identifier for the first healthcare facility and at least a portion of the information about the first clinical event, the second graphical indicator including the identifier for the second healthcare facility and at least a portion of the information about the second clinical event; and transmitting the map to the client agent application, wherein the client agent application presents the map within the graphical user interface GUI of the client agent application such that the map is displayed on the display concurrently with the GUI for the client EHR.

12. The method of claim 11, wherein the first clinical event is treatment for a first injury of the patient at the first healthcare facility, wherein the second clinical event is treatment for a second injury of the patient at the second healthcare facility.

13. The method of claim 11, wherein the first healthcare facility is a first type of healthcare facility, wherein the second healthcare facility is a second type of healthcare facility, wherein the first graphical indicator is presented in a first color assigned to the first type of healthcare facility, wherein the second graphical indicator is presented in a second color assigned to the second type of healthcare facility.

14. The method of claim 11, wherein identifying the first patient health record and the second patient health record based upon the identifier for the patient comprises executing a search over a plurality of patient health records for a plurality of patients stored in the computer-readable data store, wherein the plurality of patient health records are aggregated from a plurality of different electronic sources, wherein the search is executed based upon the identifier for the patient, and further wherein the search produces search results that include the first patient health record and the second patient health record.

15. The method of claim 11, wherein the server agent application identifies a plurality of patient health records for the patient corresponding to a plurality of clinical events that occurred at a plurality of healthcare facilities, wherein the map further comprises graphical indicators that each correspond to a different clinical event that occurred at a different healthcare facility, the method further comprising:
determining a number of times in which a designated clinical event is repeated throughout the plurality of patient health records; and
when the number of times exceeds a threshold value, causing an alert to be transmitted to the client agent application, wherein the client agent application presents the alert within the GUI for the client agent application, the alert indicating that the number of times in which the designated clinical event has occurred has exceeded the threshold value.

16. The method of claim 11, wherein the client agent application receives a selection of the first graphical indicator included in the map, thereby causing the client agent application to transmit an identifier for the first patient health record to the server agent application, the method further comprising:
responsive to receiving the identifier for the first patient health record, retrieving the first patient health record; and
transmitting the first patient health record to the client agent application, wherein the client agent application presents the first patient health record within the GUI for of the client agent application.

17. The method of claim 11, wherein server agent application transmits the request for the map to the mapping computing system in response to receiving an indication that a selectable button presented within the GUI of the client agent application has been selected by a user of the client computing device.

18. A non-transitory computer-readable medium comprising instructions that, when executed by a processor, cause the processor to perform acts comprising:
receiving, from a client agent application that is executing on a client computing device, an identifier for a patient, wherein the client computing device executes a client electronic health records application (EHR), wherein a graphical user interface (GUI) of the client agent application is displayed concurrently on a display of the client computing device with a GUI of the client EHR, and further wherein the identifier for the patient is received from the client agent application due to the GUI of the client EHR displaying the identifier for the patient on the display of the client computing device;
responsive to receiving the identifier for a patient and based upon the identifier for the patient, identifying a first patient health record for the patient and a second patient health record for the patient from a computer-readable data store that comprises health records for patients, wherein the first patient health record comprises:
an identifier for a first healthcare facility at which a first clinical event of the patient occurred; and
information about the first clinical event;
wherein the second patient health record comprises:
an identifier for a second healthcare facility at which a second clinical event of the patient occurred; and
information about the second clinical event;
transmitting the identifier for the first healthcare facility and the identifier for the second healthcare facility to a mapping computing system;
receiving, from the mapping computing system, a map of an area encompassing both the first healthcare facility and the second healthcare facility, wherein the map is retrieved by the mapping computing system based upon the identifier for the first healthcare facility and the identifier for the second healthcare facility, wherein the map includes a first marker that marks a location of the first healthcare facility on the map and a second marker that marks a location of the second healthcare facility on the map;
responsive to receiving the map from the mapping computing system, updating the map to include:
a first graphical indicator positioned to visually correspond to the first marker; and
a second graphical indicator positioned to visually correspond to the second marker, wherein the first graphical indicator includes the identifier for the first healthcare facility and at least a portion of the information about the first clinical event, and further wherein the second graphical indicator includes the identifier for the second healthcare facility and at least a portion of the information about the second clinical event; and
causing the updated map to be displayed within the GUI of the client agent application on the display of the client computing device such that the map is displayed concurrently with the GUI for the client EHR application.

19. The non-transitory computer-readable medium of claim 18, wherein causing the updated map to be displayed on the display of the client computing device comprises transmitting the map to the client agent application.

20. The non-transitory computer-readable medium of claim 19, wherein the first patient health record was generated by a first EHR application, wherein the second patient health record was generated by a second EHR application.

* * * * *